US011538559B2

(12) United States Patent
Vrouwenvelder et al.

(10) Patent No.: US 11,538,559 B2
(45) Date of Patent: Dec. 27, 2022

(54) USING MACHINE LEARNING TO EVALUATE PATIENTS AND CONTROL A CLINICAL TRIAL

(71) Applicant: International Business Machines Corporation, Armonk, NY (US)

(72) Inventors: Adrian Vrouwenvelder, Chapel Hill, NC (US); Stephen Alan Carraway, Durham, NC (US); Kimberly Diane Kenna, Cary, NC (US); John Hefferman, Durham, NC (US)

(73) Assignee: Merative US L.P., Ann Arbor, MI (US)

( * ) Notice: Subject to any disclaimer, the term of this patent is extended or adjusted under 35 U.S.C. 154(b) by 247 days.

(21) Appl. No.: 15/931,748

(22) Filed: May 14, 2020

(65) Prior Publication Data

US 2021/0358576 A1    Nov. 18, 2021

(51) Int. Cl.
*G16H 10/20* (2018.01)
*G16H 40/20* (2018.01)
(Continued)

(52) U.S. Cl.
CPC .......... *G16H 10/20* (2018.01); *G06N 3/0454* (2013.01); *G16H 40/20* (2018.01); *G16H 50/70* (2018.01);
(Continued)

(58) Field of Classification Search
CPC ........ G16H 10/00–80/00; G06N 3/00–99/007; G06Q 10/00–2250/905; G08G 1/00–99/00
See application file for complete search history.

(56) References Cited

U.S. PATENT DOCUMENTS 7,415,447 B2   8/2008  Shilfman et al.
8,032,545 B2  10/2011  Setimi
(Continued)

FOREIGN PATENT DOCUMENTS

WO       2015102844 A1     7/2015
WO       2019182297 A1     9/2019
WO    WO-2020033754 A1 *   2/2020  ............. G16H 10/20

OTHER PUBLICATIONS

Getz et al., "Assessing Patient Participation Burden Based on Protocol Design Characteristics," Therapeutic Innovation & Regulatory Science 2020, vol. 54(3) 598-604. (Year: 2020).*
(Continued)

*Primary Examiner* — Jonathon A. Szumny
(74) *Attorney, Agent, or Firm* — Edell, Shapiro & Finnan, LLC

(57) ABSTRACT

A method, computing platform, and computer program product are provided for monitoring a clinical trial. A computer platform receives, for the clinical trial, study design information including a set of parameters and corresponding parameter values related to travel constraints of a subject for the clinical trial. The computer platform applies the study design information and the corresponding parameter values to a trained machine learning model to calculate a predicted travel score indicative of a travel burden for the subject. When the travel score fails to satisfy a travel score threshold, the computer platform determines at least one suggestion for adjusting the travel score and the at least one suggestion is output. The computer platform outputs the predicted travel score.

20 Claims, 8 Drawing Sheets

(51) Int. Cl.
*G16H 50/70* (2018.01)
*G06N 3/04* (2006.01)
*G06Q 50/30* (2012.01)
*G08G 1/01* (2006.01)
*G06N 20/00* (2019.01)
*G06N 5/04* (2006.01)
*G16H 50/20* (2018.01)

(52) U.S. Cl.
CPC .............. *G06N 5/04* (2013.01); *G06N 20/00* (2019.01); *G06Q 50/30* (2013.01); *G08G 1/0141* (2013.01); *G16H 50/20* (2018.01)

(56) References Cited

U.S. PATENT DOCUMENTS

| | | | |
|---|---|---|---|
| 8,386,416 B2 | 2/2013 | Levin, II et al. | |
| 8,793,145 B2 | 7/2014 | Kahn et al. | |
| 9,600,637 B2 | 3/2017 | Harder et al. | |
| 10,255,273 B2 | 4/2019 | Chakraborty et al. | |
| 10,366,781 B1 | 7/2019 | Menon et al. | |
| 11,328,796 B1* | 5/2022 | Jain | G16H 10/20 |
| 2005/0256380 A1* | 11/2005 | Nourie | G16H 40/67 |
| | | | 600/300 |
| 2006/0036471 A1 | 2/2006 | Sanjay-Gopal et al. | |
| 2006/0129326 A1 | 6/2006 | Braconnier et al. | |
| 2006/0282244 A1 | 12/2006 | Chotai et al. | |
| 2007/0294111 A1 | 12/2007 | Settimi | |
| 2009/0112618 A1 | 4/2009 | Johnson et al. | |
| 2010/0114594 A1 | 5/2010 | Schultz | |
| 2010/0250273 A1* | 9/2010 | Li | G06Q 10/00 |
| | | | 705/2 |
| 2014/0214441 A1* | 7/2014 | Young | G16H 10/20 |
| | | | 705/2 |
| 2014/0278469 A1 | 9/2014 | Secci | |
| 2014/0324553 A1 | 10/2014 | Rosenberg | |
| 2014/0344208 A1 | 11/2014 | Ghasemzadeh et al. | |
| 2014/0358571 A1* | 12/2014 | Geleijnse | G16H 40/20 |
| | | | 705/2 |
| 2015/0220868 A1 | 8/2015 | Elashoff | |
| 2016/0042155 A1* | 2/2016 | Li | G16H 10/20 |
| | | | 705/2 |
| 2016/0203296 A1* | 7/2016 | Bound | G16H 10/20 |
| | | | 705/3 |
| 2018/0039763 A1 | 2/2018 | Tidor | |
| 2018/0181573 A1 | 6/2018 | Zhao | |
| 2018/0301209 A1* | 10/2018 | Kim | G16H 20/10 |
| 2018/0310890 A1* | 11/2018 | Li | G06F 16/951 |
| 2019/0080785 A1 | 3/2019 | Li | |
| 2019/0131001 A1* | 5/2019 | Fox | G06Q 10/063 |
| 2019/0206521 A1* | 7/2019 | Walpole | G16H 15/00 |
| 2019/0306093 A1 | 10/2019 | Schilling et al. | |
| 2019/0311787 A1* | 10/2019 | Graiver | G16H 10/60 |
| 2020/0042923 A1* | 2/2020 | Zhou | G16H 20/10 |
| 2020/0211680 A1* | 7/2020 | Sablinski | G16H 20/00 |
| 2021/0357769 A1 | 11/2021 | Vrouwenvelder et al. | |
| 2021/0357778 A1 | 11/2021 | Vrouwenvelder et al. | |

OTHER PUBLICATIONS

Borno et al., "At What Cost to Clinical Trial Enrollment? A Retrospective Study of Patient Travel Burden in Cancer Clinical Trials," The Oncologist 2018;23:1242-1249. (Year: 2018).*

Medidate Solutions, Using Patient Burden Evaluation to Improve Clinical Trial Planning and Execution, May 2018 White Paper, pp. 1-7. (Year: 2018).*

Harrer et al., "Artificial Intelligence for Clinical Trial Design," Trends in Pharmacological Sciences, Aug. 2019, vol. 40, No. 8 (Year: 2019).*

"Study Shows that with Clinical Trial Participation Comes the Burden of Travel," ClinEdge Staff, https://clin-edge.com/news/study-shows-that-with-clinical-trial-participation-comes-the-burden-of-travel (Year: 2018).*

List of IBM Patents or Patent Applications Treated as Related, filed Jun. 2, 2020.

B. Pflugeisen, et al., "Assessment of clinical trial participant patient satisfaction: a call to action", Trials 17, 483 (2016). https://doi.org/10.1186/s13063-016-1616-6, 7 pages.

* cited by examiner

USING MACHINE LEARNING TO EVALUATE PATIENTS AND CONTROL A CLINICAL TRIAL

BACKGROUND

1. Technical Field

Present invention embodiments relate to monitoring and controlling a clinical trial. In particular, the present invention embodiments relate to using a first trained machine learning model to predict a travel score related to travel for respective one or more subjects of a clinical trial and providing and/or implementing one or more suggestions for controlling the clinical trial.

2. Discussion of the Related Art

A number of factors can affect a likelihood of success for a clinical trial. One of those factors is a retention rate of patients participating in the clinical trial. As patients leave an uncompleted clinical trial, less data is available for analysis, possibly affecting reliability of results.

Factors that can affect a patient's continuing participation in a clinical trial may include, but not be limited to, a number and frequency of required visits to a clinic, the patient's level of mobility, and the patient's travel time and cost for travel to and from the clinic. Patients who experience travel to the clinic as a great burden are less likely to remain participants in the clinical trial until completion.

SUMMARY

According to one embodiment of the present invention, a computer-implemented method for monitoring a clinical trial is provided. According to the computer-implemented method, a computer platform receives study design information for the clinical trial. The study design information includes a set of parameters and corresponding parameter values related to travel constraints of a subject for the clinical trial. The computer platform applies the study design information and the corresponding parameter values to a trained machine learning model to calculate a predicted travel score indicative of a travel burden for the subject. When the travel score fails to satisfy a travel score threshold, the computer platform determines at least one suggestion for adjusting the travel score, and outputs the at least one suggestion for adjusting the travel score. The predicted travel score also is output by the computer platform.

According to a second embodiment of the present invention, a computer platform for monitoring a clinical trial is provided. The computer platform includes at least one processor and at least one memory connected with the at least one processor. The at least one processor is configured to receive study design information for the clinical trial. The study design information includes a set of parameters and corresponding parameter values related to travel constraints of a subject for the clinical trial. The study design information and the corresponding parameter values are applied to a trained machine learning model to calculate a predicted travel score indicative of a travel burden for the subject. When the travel score fails to satisfy a travel score threshold, the computer platform determines at least one suggestion for adjusting the travel score and outputs the at least one suggestion. The computer platform also outputs the predicted travel score.

According to a third embodiment of the present invention, a computer program product is provided for monitoring a clinical trial. The computer program product includes one or more computer readable storage media having program instructions collectively stored on the one or more computer readable storage media. The program instructions are executed by at least one process of a computer platform. Execution of the program instructions causes the computer platform to receive study design information for the clinical trial. The study design information includes a set of parameters and corresponding parameter values related to travel constraints of a subject for the clinical trial. The computer platform also is caused to apply the study design information and the corresponding parameter values to a trained machine learning model to calculate a predicted travel score indicative a travel burden for the subject. When the travel score fails to satisfy a travel score threshold, the computer platform is caused to determine at least one suggestion for adjusting the travel score, and output the at least one suggestion. The computer platform is also caused to output the predicted travel score.

BRIEF DESCRIPTION OF THE DRAWINGS

Generally, like reference numerals in the various figures are utilized to designate like components.

DETAILED DESCRIPTION

In various embodiments of the present invention, a machine learning model is trained to evaluate a travel burden (e.g., an ease or difficulty of travel) for candidate or actual patients for a clinical trial and to predict a travel score for one or more of the candidate or actual patients indicative of the travel burden (e.g., an amount of ease related to travel) for each of the one or more of the candidate or actual patients based on a set of parameters and corresponding values.

Embodiments may include a number of different input parameters. Example input parameters that may help to predict a travel score for a patient or candidate patient for a clinical trial may include, but not be limited to, an age of the patient or candidate patient age, a level of mobility for the patient or candidate patient, one or more modes of travel the patient or candidate patient may use to travel to and from a clinical trial facility, whether the patient or candidate patient must visit the clinical trial facility during the clinical trial, a number of clinical trial visits required by the patient or candidate patient during the clinical trial, a distance to travel for the patient or candidate patient to reach the clinical trial facility, an expected amount of travel time for the patient or candidate patient to travel to and from the clinical trial facility, an expected travel cost for the patient or candidate patient to travel to and from the clinical trial facility, a level of family income, traffic density related to travel by the patient or candidate patient to and from the clinical trial facility, whether the patient or candidate patient has residential computer access to clinical trial data collection resources, whether the patient or candidate patient owns a telephone, and climate for a given locale of the clinical trial facility during the clinical trial.

Figure 1:
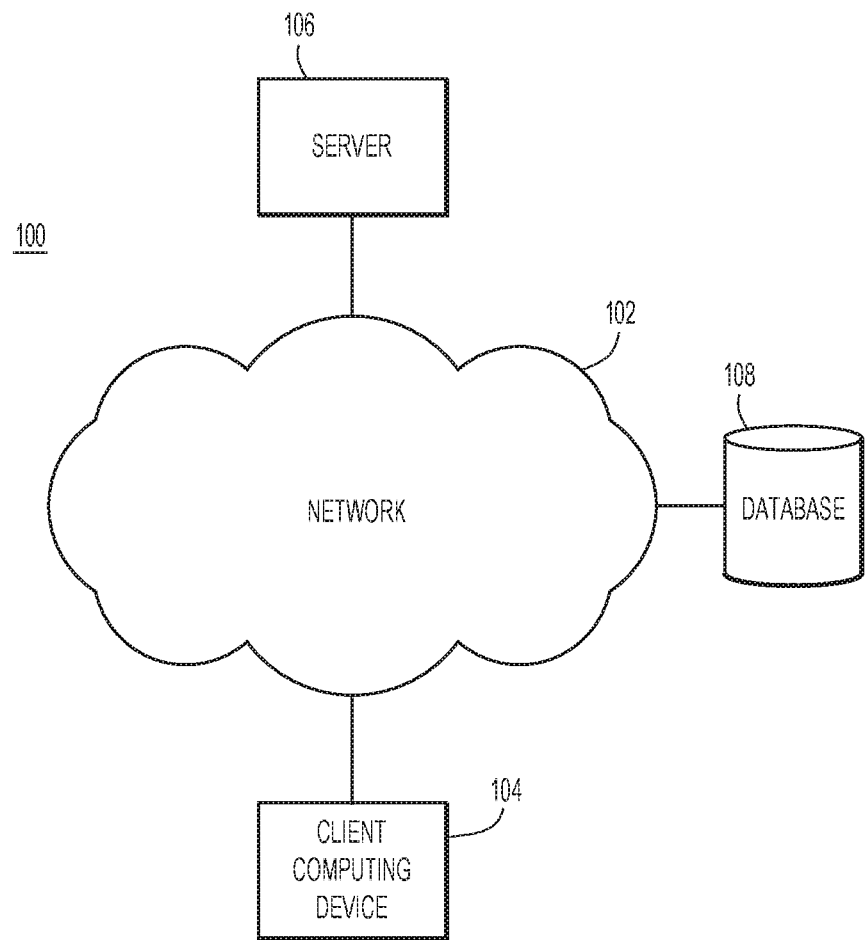
FIG. 1 illustrates an example operating environment according to various embodiments.

An example environment 100 for use with present invention embodiments is illustrated in FIG. 1. Specifically, environment 100 includes one or more client or end-user computing devices 104, a computing platform, which may include one or more servers 106, and a database management system 108, which may be included as part of one or more servers 106 or may be executing on a separate system connected to network 102. Server 106, client computing device 104, and database management system 108 may be remote from each other and may communicate over a network 102. Network 102 may be implemented by any number of any suitable communications media (e.g., wide area network (WAN), local area network (LAN), Internet, Intranet, etc.). Alternatively, server 106, client computing device 104, and database management system 108 may be local to each other and may communicate via any appropriate local communication medium (e.g., local area network (LAN), hardwire, wireless link, Intranet, etc.).

Client computing device 104 enables a user such as, for example, a clinical study designer, to submit input parameters and corresponding parameter values for a clinical trial. The input parameters and corresponding values may be provided to client computing device 104 by the user via a user interface, which may be a graphical user interface, a textual user interface, a speech recognition user interface, or other user interface. The input parameters and the corresponding values may be provided by client computing device 104 to server 106 via network 102. Server 106 may receive the input parameters and the corresponding values and may apply the input parameters and the corresponding values to a machine learning model trained to predict a travel score for each respective patient or candidate patient for the clinical trial. Server 106 may provide client computing device 104 output from the machine learning model for presentation to the user via client computing device 104. The output may include, for example, the predicted travel score for the each respective patient or candidate patient presented in a graphical format. Other embodiments may present the output in other forms such as, for example, displayed text and computer-generated speech, as well as other forms.

Database management system 108 may store various information for analysis by the machine learning model such as, for example, the input parameters and their corresponding values as well as other information that may be evaluated by one or more other machine learning models. Database management system 108 may be implemented by any conventional or other database or storage unit, may be local to or remote from server 106 and client computing device 104, and may communicate via any appropriate communication medium (e.g., local area network (LAN), wide area network (WAN), Internet, hardwire, wireless link, Intranet, etc.).

The client computing device 104 may present a graphical user interface (e.g., GUI, etc.) or other user interface (e.g., command line prompts, menu screens, etc.) to solicit information from the user pertaining to the clinical trial input parameters and the corresponding parameter values, and may provide results from applying the input parameters and the corresponding parameter values to one or more other machine learning models.

Figure 2:
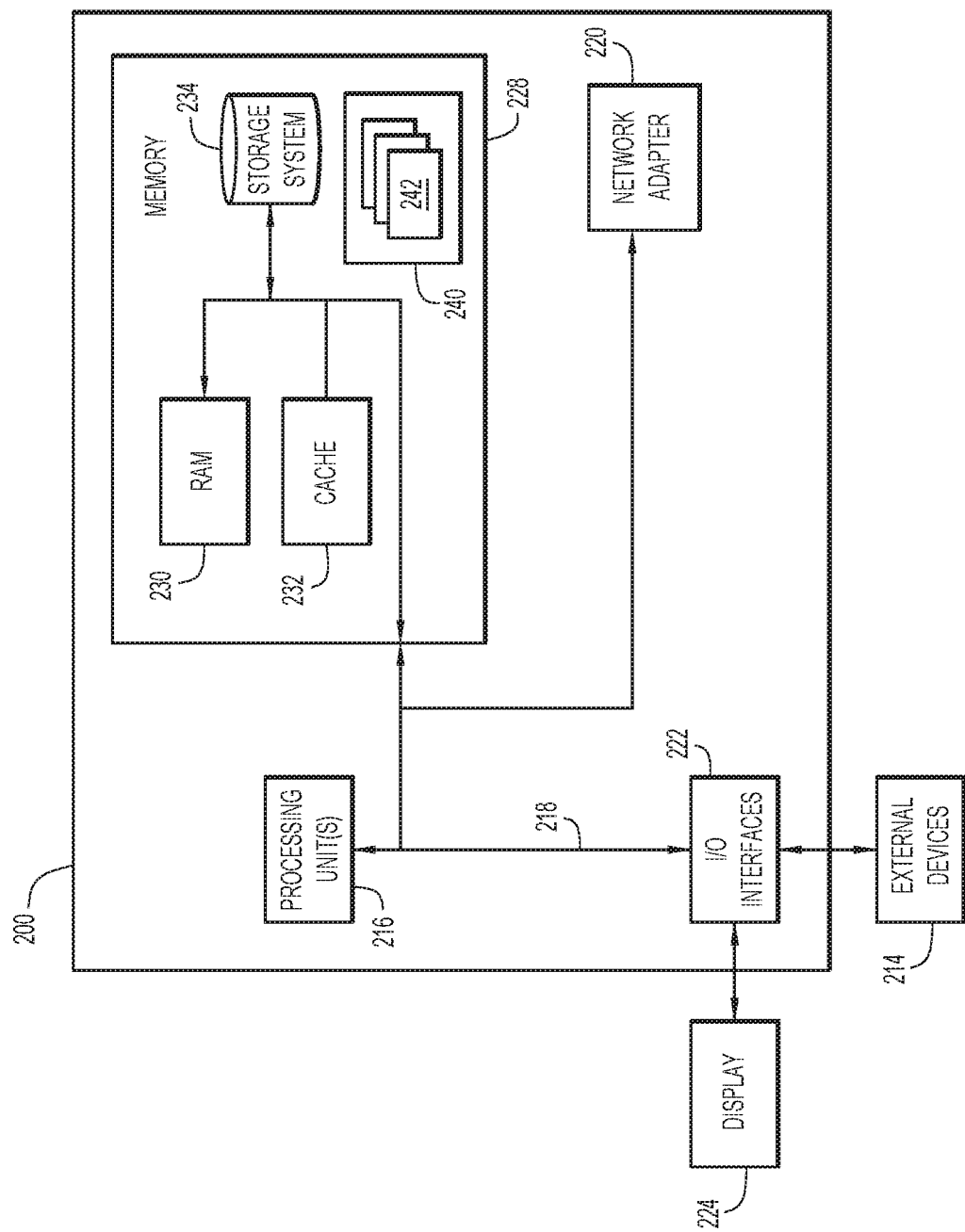
FIG. 2 is a functional block diagram of an example computer platform that may implement a server or a client computing device according to various embodiments.

Referring now to FIG. 2, a schematic of an example computer system 200 is shown, which may implement any of server 106 and client computer device 104 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232. Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
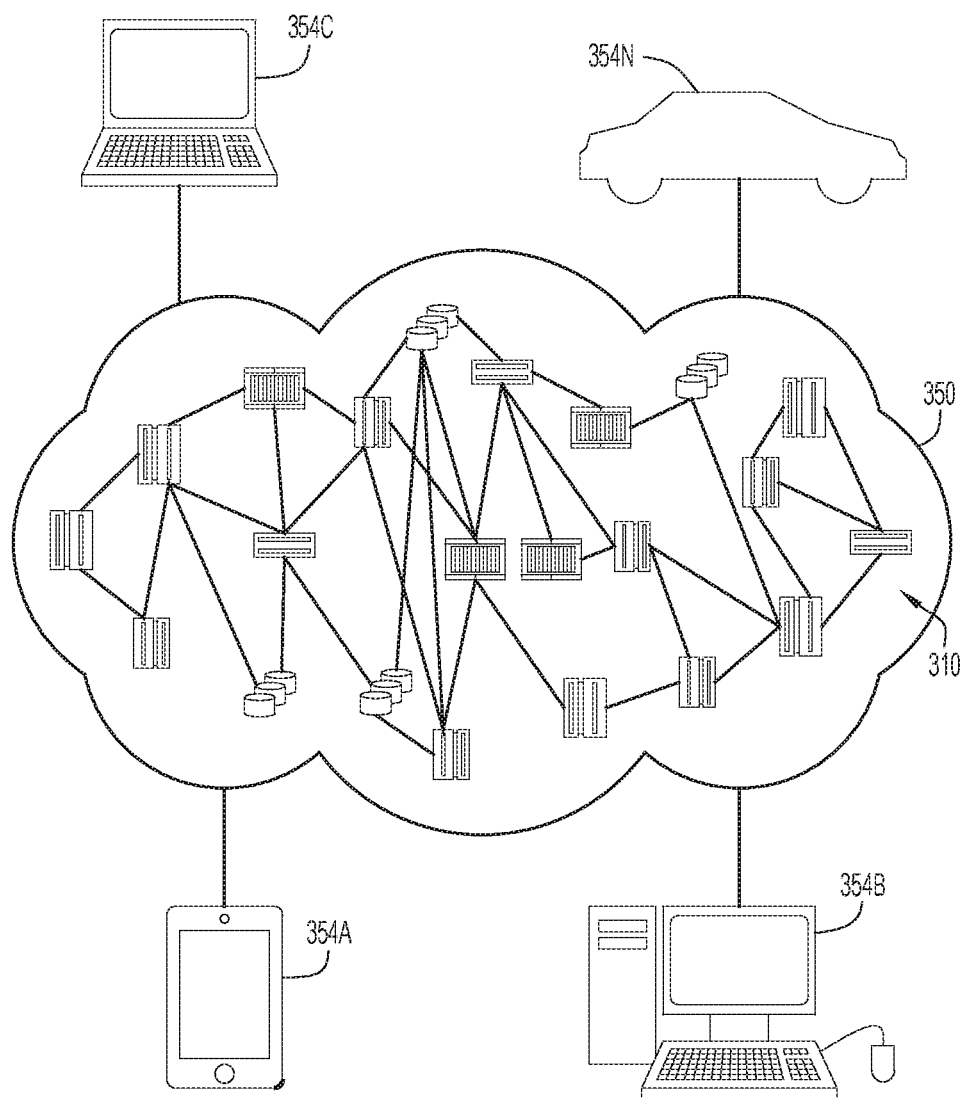
FIG. 3 illustrates an example cloud computing environment according to some embodiments of the invention.

Referring now to FIG. 3, an illustrative cloud computing environment 350 is depicted. As shown, cloud computing environment 350 includes one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
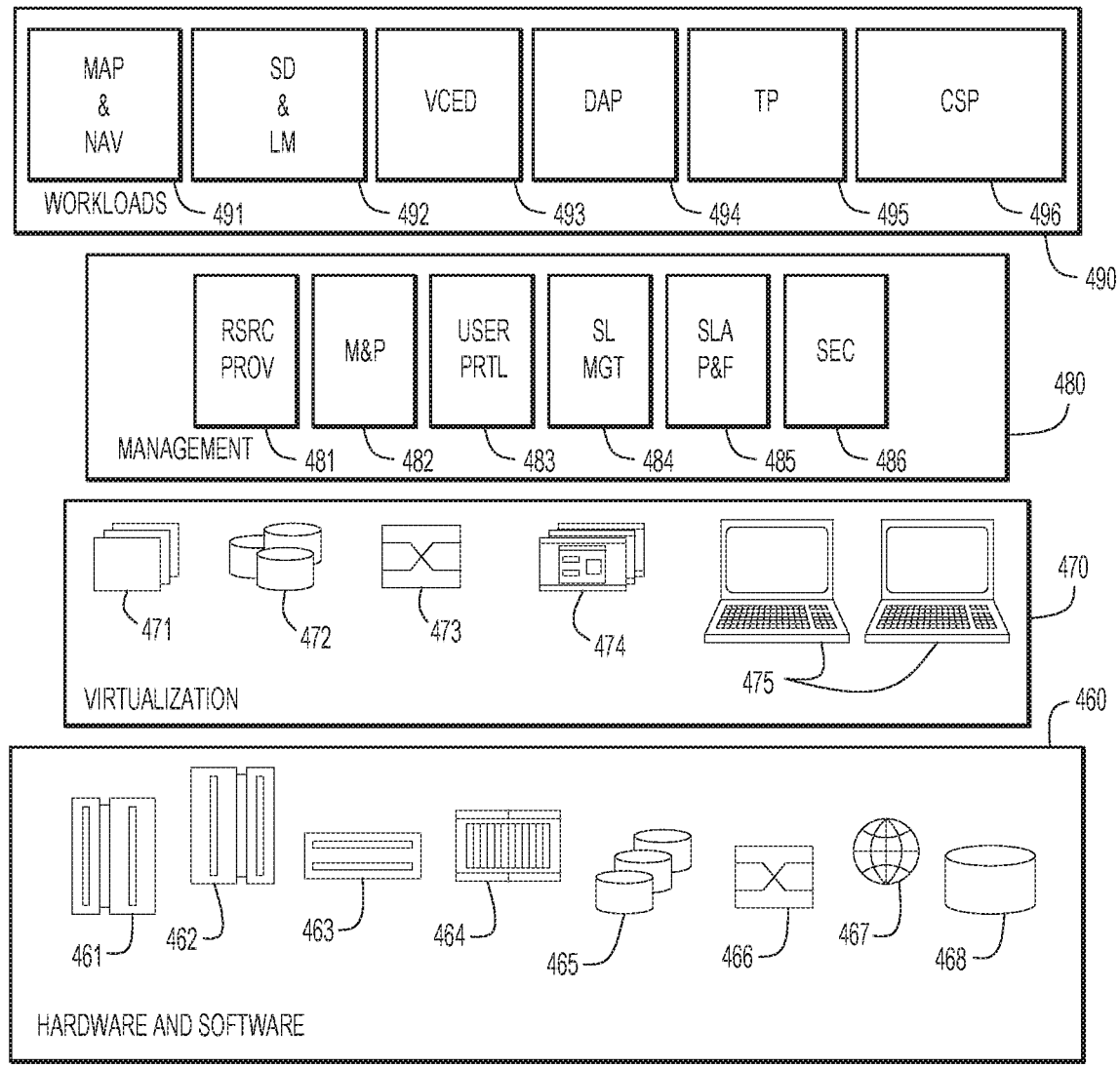
FIG. 4 illustrates an example set of functional abstraction layers that may be provided by the example cloud computing environment of FIG. 3, according to some embodiments.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example, management layer 480 may provide the functions described below. Resource provisioning 481 provides dynamic procurement of computing resources and other resources that are utilized to perform tasks within the cloud computing environment. Metering and pricing 482 provide cost tracking as resources are utilized within the cloud computing environment, and billing or invoicing for consumption of these resources. In one example, these resources may include application software licenses. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA. Security (SEC) 486 provides identity verification for cloud consumers and tasks, as well as protection for data and other resources.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; and clinical study processing (CSP) 496 for receiving input parameters and corresponding values for a clinical trial and for predicting a respective travel score for each one or more respective candidate or actual patient for the clinical trial.

Figure 5:
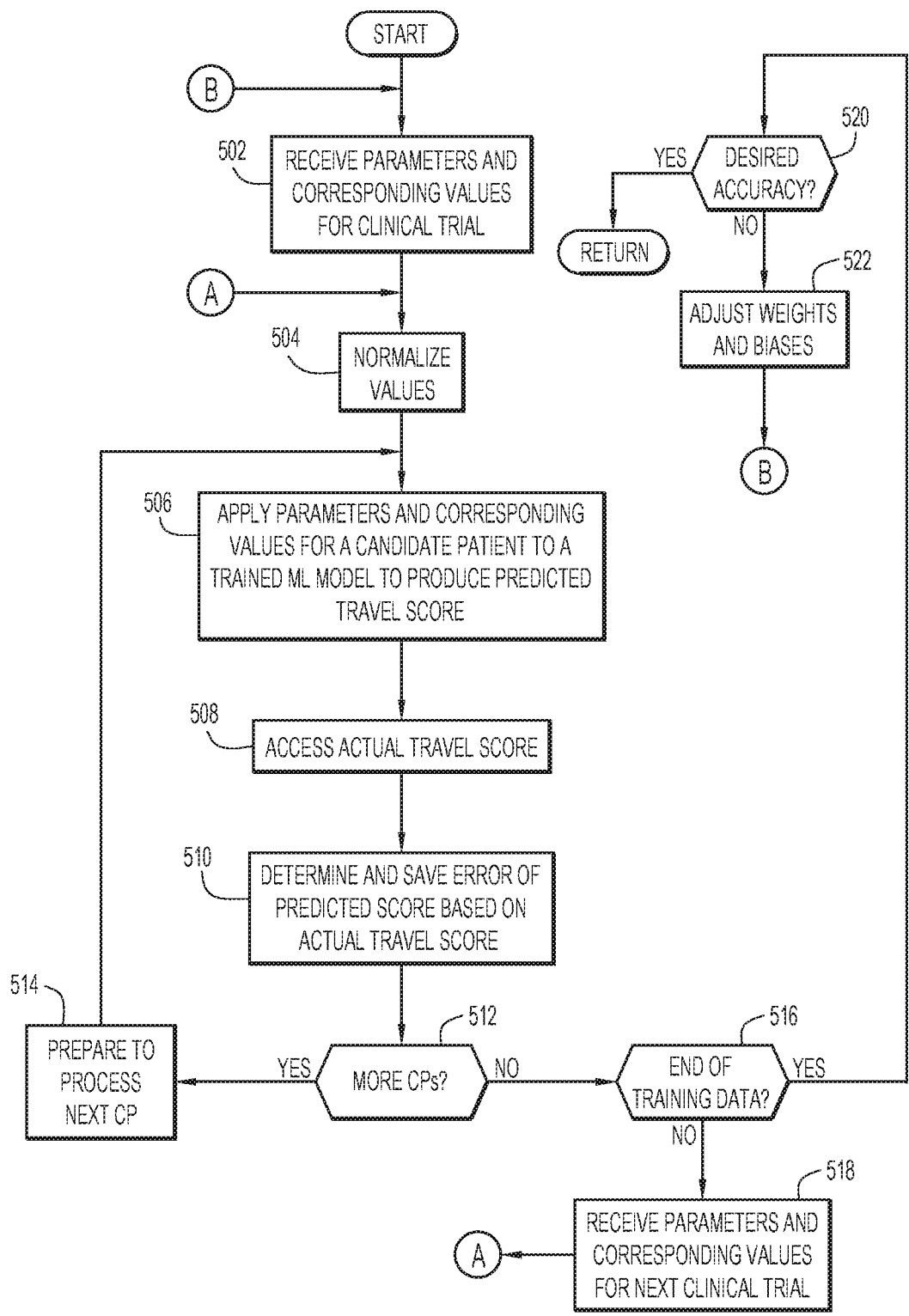
FIG. 5 is a flowchart of an example process for training a machine learning model for predicting a travel score according to embodiments of the present invention.

FIG. 5 is a flowchart of an example process, in various embodiments, for training a machine learning model to predict a travel score for each candidate or actual patient for a clinical trial. This process is known as supervised machine learning. Training data includes parameters and corresponding parameter values of actual clinical trials and actual travel scores related to the patients participating in the clinical trials. In some embodiments, a travel score may be in a range of 0 to 100, where 0 is a worst travel score indicative of an impossible travel burden for a clinical trial participant and 100 is a best travel score indicative of a most easy and pleasant travel experience for the clinical travel participant. In other embodiments, the travel score may be in a range of 0.00 to 1.00, where 0.00 is the worst travel score and 1.00 is the best travel score. Other ranges for a travel score may be employed in other embodiments of the present invention.

An example machine learning model for predicting respective travel scores for respective patient participants or candidate patient participants based on input parameters and corresponding parameter values and which uses regression may result in the machine learning model of $y1=B0_1+B1_1 \times x1+B2_1 \times x2+B3_1 \times x3+ \ldots Bn_1 \times xn$, where y1 is a travel score for the patient participant or the candidate patient participant in the clinical trial; $B0_1$ is an offset, $B1_1$ through $Bn_1$ are coefficients, and x1 through xn represent the input parameter values represented as numerical values. $B0_1$ through $Bn_1$ are derived through training the first machine learning model using a supervised machine learning technique.

The process may begin by receiving parameters and corresponding parameter values of a clinical trial included in the training data (act 502). In some embodiments, the machine learning model may include a regression algorithm such as, for example, a linear regression algorithm. Further, the machine learning model of some embodiments may include a convolutional neural network (CNN). In other embodiments, another algorithm may be included in the machine learning model. The machine learning model may include weights and a bias to be applied to values of at least some of the input parameters to calculate a predicted travel score for each patient or candidate patient of a clinical trial. The respective weights and the respective bias included in each of the one or more machine learning models may be set to predefined values initially such as, for example, zero or another value.

The machine learning model may be trained based on actual clinical trials with known parameters and corresponding values as well as a respective known travel score for each patient or candidate patient of the clinical trial. To train a machine learning model, training data may include data from a number of actual clinical trials such as, for example, 10,000 clinical trials or another number of clinical trials.

After receiving the parameters and corresponding parameter values of a clinical trial, the parameter values may be normalized (act 504). Alternatively, instead of normalizing values of the input parameters during the training process, the values of the input parameters may be normalized before the training process.

Next, the received input parameter values, which include travel-related input parameter values for a respective patient or candidate patient, may be applied to the machine learning model to produce a predicted travel score associated with the patient or candidate patient (act 506). After producing the predicted travel score, an actual travel score for the patient or candidate patient of the clinical trial may be accessed (act 508) and an error amount may be determined and saved based on a difference between the actual travel score and the predicted travel score (act 510).

A determination then may be made regarding whether there are any more patients or candidate patients for the clinical trial for whom a travel score is to be predicted (act 512). If there are more patients or candidate patients, the process may prepare to process a next patient or candidate patient to predict an associated travel score (act 514). Acts 506-512 again may be performed.

If, during act 512, no additional patients or candidate patients for the clinical trial are determined to exist, a determination may then be made regarding whether an end of the training data is reached (act 516) and, if not, a next set of parameters and corresponding values for a next clinical trial may be received from the training data (act 518). Acts 504-514 then may be performed again.

If, during act 516, the end of the training data is determined to have been reached, then a determination may be made regarding whether the predicted travel scores are within a desired range of accuracy (act 520). If the predicted scores are determined not to be within the desired range of accuracy, then the weights and the biases for the machine learning model may be adjusted to improve accuracy (act 522). The process may then continue processing by starting again with act 502.

Figure 6:
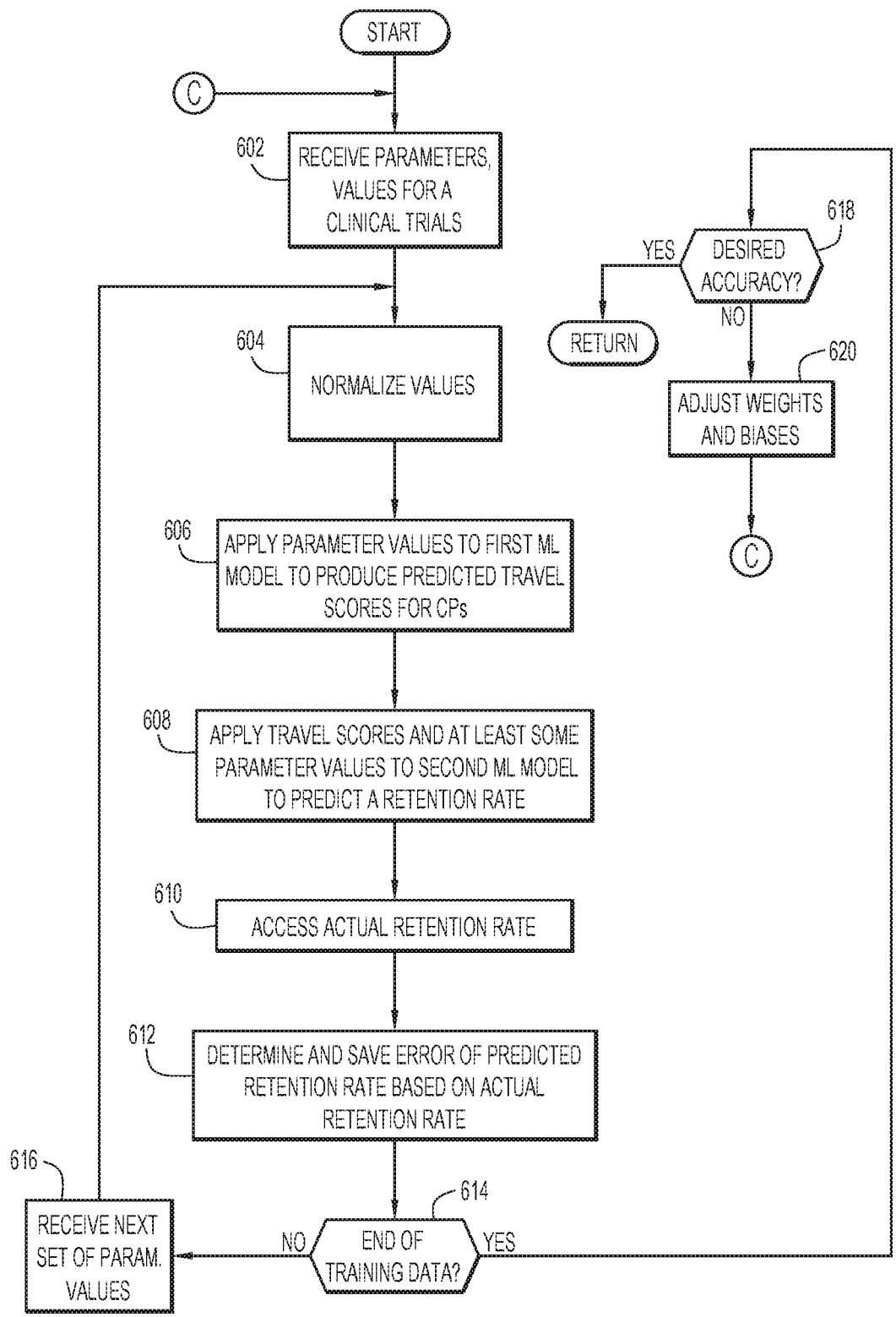
FIG. 6 is a flowchart illustrating an example process for training a second machine learning model to predict a retention rate for a clinical trial according to some embodiments of the present invention.

FIG. 6 is a flowchart illustrating an example process by which a second machine learning model may be trained to predict an overall success score. Training data may include the parameters and the corresponding values used to train a machine learning model for predicting travel scores as well as other parameters and other corresponding parameter values, which are collectively referred to, in FIG. 6, as input parameters and parameter values. Input to the second machine learning model may include the predicted travel scores predicted by the first machine learning model for each patient or candidate patient of a clinical trial.

The process may begin with server 106 receiving the input parameters and the corresponding parameter values for a clinical trial (act 602). At least some of the received parameter values then may be normalized (act 604). Alternatively, the at least some of the received parameter values in the training data set may have previously been normalized such that normalization may not be performed during training.

The process then may apply the normalized parameter values to a first trained machine learning model to produce a predicted travel score for each patient or candidate patient of the clinical trial (act 606). Server 106 may then apply the predicted travel scores and at least some of the normalized parameter values to a second machine learning model to produce a predicted retention rate for the clinical trial (act 608). In some embodiments, the predicted retention rate may be in a range from 0 to 100 corresponding, respectively, to 0% retention rate and 100% retention rate. In other embodiments, other ranges may be employed such as, for example, 0.00 to 1.00, which may correspond, respectively, to retention rates of 0% and 100%.

Next, the process may access an actual retention rate for the clinical trial included in the training data (act 610) and may determine and save an amount of error of the predicted retention rate based on the actual retention rate (act 612).

The process then may determine whether an end of the training data has been reached (act 614). If the end of the training data has not been reached, then the process may receive, or input, a next set of parameters and corresponding parameter values for a next clinical trial (act 616). Acts 604-614 again may be repeated.

If, during act 614, the process determines that the end of the training data has been reached, then the process may determine whether the predicted retention rate has reached a desired level of accuracy (act 618). If the desired level of accuracy has been reached, then the process is completed. Otherwise, weights and a bias with respect to the second machine learning model may be adjusted (act 620) and the process may begin again with act 602.

In some embodiments, retention rate along with other parameters and corresponding parameter values may be applied to a third trained machine learning model to predict an overall success score for a clinical trial. A range of values for the predicted overall success score may be from 0 to 100, respectively, corresponding to 0% and 100%. Other ranges of values for the predicted overall success score may be employed in other embodiments.

As an example of other machine learning models for making predictions regarding a clinical trial, a fourth machine learning model may be trained to predict a data quality score for a clinical trial based on input parameter values including an indication of a level of complexity of survey questions for patients in the clinical trial, whether a medical focus of each clinical trial visit is related to a same medical focus as a previous clinical trial visit, etc.

Continuing with the example, a fifth machine learning model may be trained to predict a participant recruitment score. An actual participant recruitment score may be based on a number of candidate participants asked to participate in a clinical trial and a number of those candidate participants that agreed to participate in the clinical trial. The fifth machine learning model may be trained using input parameter values related to various characteristics of candidate participants from actual clinical trials having known actual participant recruitment scores.

A sixth machine learning model may be trained to predict a participant retention rate based on input parameter values including characteristics of candidate participants that may affect whether a candidate participant remains in the clinical trial until completed.

A machine learning model for predicting an overall success score may input the predicted data quality score, the predicted participant retention score, and the predicted participant recruitment score, and may include other input parameter values such as, for example, parameter values indicating a seriousness of a patient's condition, whether a patient suffers from a cognitive impairment and a level of the cognitive impairment, etc. to predict the overall success score for the clinical trial.

In alternative embodiments, an average travel score may be calculated, based on a predicted travel score of each patient or candidate patient of the clinical trial, and provided to a trained machine learning model to calculate a predicted overall clinical trial success score for the clinical trial.

In other embodiments, the above mentioned example machine learning models for making various predictions may be used in a number of different ways. For example, predicting a data quality score for a clinical trial may provide a designer of a clinical trial with information that can be used to design an improved clinical trial with more accurate and reliable data quality. Similarly, a machine learning model trained to predict a participant recruitment score may be helpful to a clinical trial designer for determining characteristics of candidate patients who are more likely to agree to participate in the clinical trial. Further, a machine learning model to predict a participant retention rate may be helpful to a clinical trial designer with respect to designing a clinical trial such that participants are more likely to remain in the clinical trial until conclusion of the clinical trial.

Figure 7:
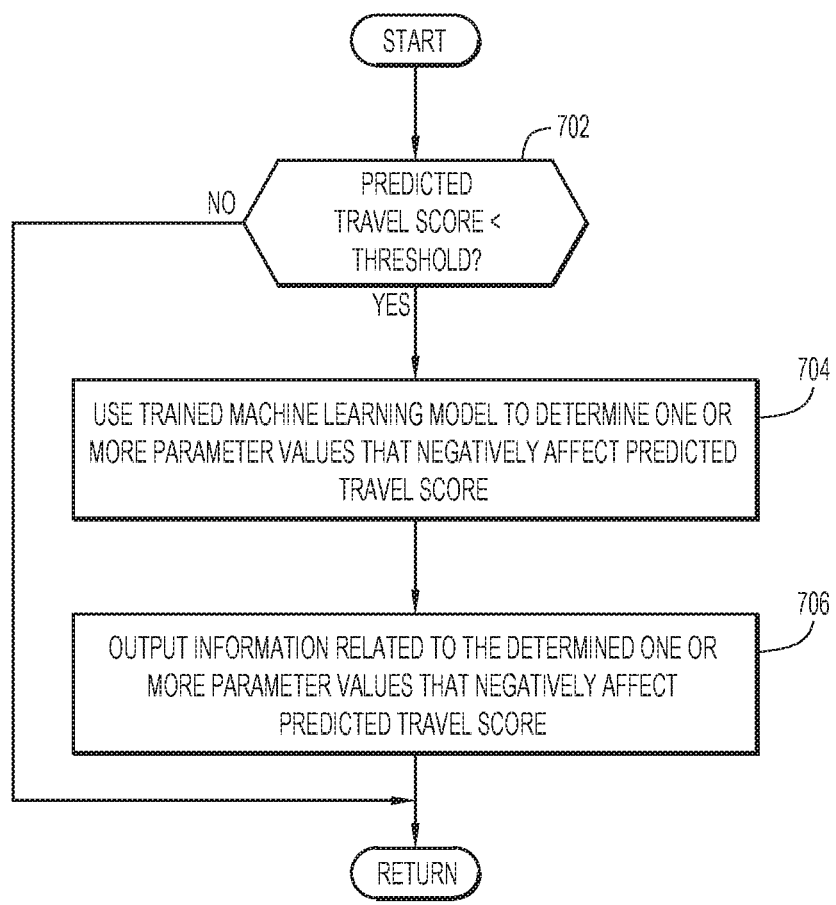
FIG. 7 illustrates a flowchart of an example process for predicting a travel score and determining and/or implementing one or more suggestions for controlling the clinical trial according to some embodiments of the present invention.

Once a machine learning model is trained to predict travel scores for patients or candidate patients of a clinical trial, the trained machine learning model may be used to determine suggestions, or recommendations, for improving a travel score. FIG. 7 is a flowchart of an example process for determining one or more suggestions for improving a travel score based on the trained machine learning model for predicting the travel score. The process may be called after predicting a travel score for a patient or a candidate patient of a clinical trial.

The process may begin with server 106 determining whether the predicted travel score is less than a threshold value (act 702). If the predicted travel score is determined not to be less than the threshold value, then the process may be completed. Otherwise, the trained machine learning model for predicting a travel score may be used to determine which one or more parameter values are negatively affecting the predicted travel score (act 704). The process then may output information related to the determined one or more parameter values that negatively affect the predicted travel score (act 706).

Based on the particular parameter values that negatively affect the travel score, accommodations may be made that may reduce the negative affect of the particular parameter values. As an example, if input parameter values indicate that the patient or candidate patient is not very mobile, the clinical trial would require the patient or candidate patient to travel to a clinical trial facility several times during the clinical trial, and the patient or candidate patient has residential computer access to clinical trial data collection resources, then the information output during act 706 may state that the patient is not very mobile and may suggest that the travel requirement for this patient or candidate patient be reduced or eliminated, if possible, and that patient data for this patient or candidate patient may be collected remotely by having the patient or candidate patient provide data for collection via his/her computer.

In an alternative embodiment, if an accommodation can be made for a patent or candidate patient such that the negative affect of the particular parameter values can be reduced or eliminated, a suggestion may be output, during act 706, and a user may be asked whether the accommodation should be automatically made to the clinical trial for the patient or candidate patient. Continuing with the example above, in addition to outputting the information regarding the one or more parameter values that negatively affect the travel score and the suggestion, the output may prompt the user to indicate whether he would like to implement the suggestion automatically. If the user replies positively, the clinical trial may be automatically adjusted to accommodate the patient or candidate patient to eliminate or reduce his/her clinical trial facility visits.

Figure 8:
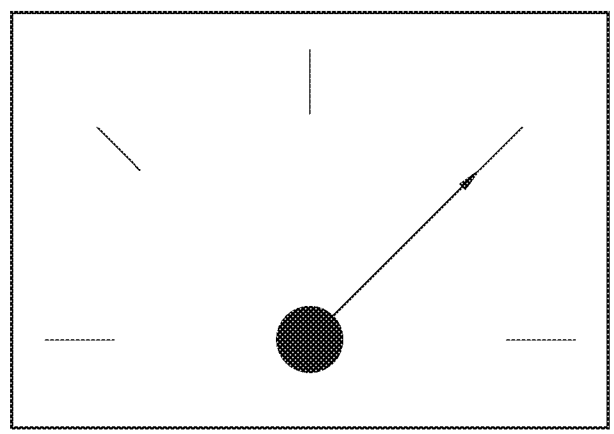
FIG. 8 illustrates an example graphical display of a predicted travel score for a subject of a clinical trial according to some embodiments of the present invention.

According to some embodiments, server 106 may output a predicted travel score to client computing device 104 such that the predicted travel score may be presented to a user of client computing device 104 via a graphical display. The predicted travel score may be presented in a form that resembles a fuel gauge in an automobile. FIG. 8 shows an example predicted travel score as being about 75% or 0.75 via a graphical display.

A clinical trial may be conducted virtually (e.g., on a computer system and/or network) and/or physically for any desired item (e.g., medication, device, etc.). It will be appreciated that the embodiments described above and illustrated in the drawings represent only a few of the many ways of evaluating parameter values for a given set of clinical trial parameters to predict a travel score.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, profile generation module, profile comparison module, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information (e.g., parameters and parameter values, etc.). The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein and in the claims, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for monitoring a clinical trial comprising:
    receiving, by a computer platform, study design information for the clinical trial, the study design information including a set of parameters and corresponding parameter values related to travel constraints of a subject for the clinical trial;
    creating, by the computer platform, first training data including parameter values of actual clinical trials and actual travel scores related to participants of the clinical trials;
    training, by the computer platform, a first machine learning model using the first training data, wherein the first machine learning model includes a first neural network and is trained to predict a travel score indicative of a travel burden, and wherein the travel burden indicates a level of difficulty of travel;
    applying, by the computer platform, the study design information and the corresponding parameter values to the trained first machine learning model to calculate a predicted travel score indicative of the travel burden for the subject;
    when the predicted travel score fails to satisfy a travel score threshold:
        determining, by the computer platform, at least one suggestion for adjusting the predicted travel score, and
        outputting, by the computer platform, the at least one suggestion for adjusting the predicted travel score;
    training, by the computer platform, a second machine learning model using the first training data to produce a predicted retention rate for the clinical trial, wherein the second machine learning model includes a second neural network, and training the second machine learning model includes:
        creating second training data including at least some of the first training data;
        processing the second training data by the trained first machine learning model to produce training predicted travel scores;
        creating third training data including the training predicted travel scores from the trained first machine learning model and at least some of the second training data; and
        training the second machine learning model using the third training data to predict the retention rate;
    determining, by the computer platform, the predicted retention rate for the clinical trial by producing predicted travel scores for a plurality of subjects for the clinical trial by the trained first machine learning model and processing the predicted travel scores and parameter values for the plurality of subjects by the trained second machine learning model to produce the predicted retention rate; and
    outputting, by the computer platform, the predicted travel score and the predicted retention rate.

2. The computer-implemented method of claim 1, wherein the determining the at least one suggestion for adjusting the predicted travel score further comprises:
    determining, by the computer platform, which one or more parameter values are negatively affecting the predicted travel score; and
    outputting information, by the computer platform, regarding the determined one or more parameter values.

3. The computer-implemented method of claim 1, wherein the set of parameters and the corresponding parameter values include one or more from a group of an age of the subject, a level of mobility of the subject, one or more modes of travel the subject can use to travel to and from a clinical trial facility, whether the subject must visit the clinical trial facility during the clinical trial, a number of clinical trial visits required of the subject, a distance for the subject to travel to reach the clinical trial facility, an expected amount of travel time for the subject to travel to and from the clinical trial facility, an expected travel cost for the subject to travel to and from the clinical trial facility, family income of the subject, traffic density related to travel by the subject to and from the clinical trial facility, whether the subject has residential computer access to clinical trial data collection resources, whether the subject owns a telephone, and climate for a given locale of the clinical trial facility during the clinical trial.

4. The computer-implemented method of claim 1, further comprising:
receiving, by the computer platform, a respective set of parameters and corresponding parameter values for each of the plurality of subjects for the clinical trial;
applying, by the computer platform, the corresponding parameter values for the each of the plurality of subjects and the study design information to the trained first machine learning model to calculate a respective predicted travel score indicative of a travel burden for the each of the plurality of subjects; and
applying, by the computer platform, the respective predicted travel score for the each of the plurality of subjects and at least some of the study design information to the trained second machine learning model to produce the predicted retention rate for the clinical trial.

5. The computer-implemented method of claim 4, further comprising:
applying, by the computer platform, the predicted retention rate to a third trained machine learning model to predict an overall success score of the clinical trial.

6. The computer-implemented method of claim 1, further comprising:
receiving, by the computer platform, a respective set of parameters and corresponding parameter values for each of the plurality of subjects for the clinical trial; and
applying, by the computer platform, the corresponding parameter values for the each of the plurality of subjects and the study design information to the trained first machine learning model to calculate a respective predicted travel score indicative of a travel burden for the each of the plurality of subjects;
calculating an average travel score for the plurality of subjects of the clinical trial based on each of the respective predicted travel scores; and
predicting an overall clinical trial success score based, at least partly, on the average travel score.

7. The computer-implemented method of claim 1, wherein:
the study design information is received from a second computer platform, and
a user interface of the second computer platform allows a user to enter and modify the set of parameters and the corresponding parameter values.

8. A computer platform for monitoring a clinical trial comprising:
at least one processor; and
at least one memory connected with the at least one processor, wherein the at least one processor is configured to perform:
receiving study design information for the clinical trial, the study design information including a set of parameters and corresponding parameter values related to travel constraints of a subject for the clinical trial;
creating first training data including parameter values of actual clinical trials and actual travel scores related to participants of the clinical trials;
training a first machine learning model using the first training data, wherein the first machine learning model includes a first neural network and is trained to predict a travel score indicative of a travel burden, and wherein the travel burden indicates a level of difficulty of travel;
applying the study design information and the corresponding parameter values to the trained first machine learning model to calculate a predicted travel score indicative of the travel burden for the subject;
when the predicted travel score fails to satisfy a travel score threshold:
determining at least one suggestion for adjusting the predicted travel score, and
outputting the at least one suggestion for adjusting the predicted travel score;
training a second machine learning model using the first training data to produce a predicted retention rate for the clinical trial, wherein the second machine learning model includes a second neural network, and training the second machine learning model includes:
creating second training data including at least some of the first training data;
processing the second training data by the trained first machine learning model to produce training predicted travel scores;
creating third training data including the training predicted travel scores from the trained first machine learning model and at least some of the second training data; and
training the second machine learning model using the third training data to predict the retention rate;
determining the predicted retention rate for the clinical trial by producing predicted travel scores for a plurality of subjects for the clinical trial by the trained first machine learning model and processing the predicted travel scores and parameter values for the plurality of subjects by the trained second machine learning model to produce the predicted retention rate; and
outputting the predicted travel score and the predicted retention rate.

9. The computer platform of claim 8, wherein the determining the at least one suggestion for adjusting the predicted travel score further comprises:
determining which one or more parameter values are negatively affecting the predicted travel score; and
outputting information regarding the determined one or more parameter values.

10. The computer platform of claim 8, wherein the set of parameters and the corresponding parameter values include one or more from a group of an age of the subject, a level of mobility of the subject, one or more modes of travel the subject can use to travel to and from a clinical trial facility, whether the subject must visit the clinical trial facility during the clinical trial, a number of clinical trial visits required by the subject, a distance for the subject to travel to reach the clinical trial facility, an expected amount of travel time for the subject to travel to and from the clinical trial facility, an expected travel cost for the subject to travel to and from the clinical trial facility, family income of the subject, traffic density related to travel by the subject to and from the clinical trial facility, whether the subject has residential computer access to clinical trial data collection resources, whether the subject owns a telephone, and climate for a given locale of the clinical trial facility during the clinical trial.

11. The computer platform of claim 8, wherein the at least one processor is further configured to perform:
receiving a respective set of parameters and corresponding parameter values for each of the plurality of subjects for the clinical trial;

applying the corresponding parameter values for each of the plurality of subjects and the study design information to the trained first machine learning model to calculate a respective predicted travel score indicative of a travel burden for the each of the plurality of subjects; and applying the respective predicted travel score for the each of the plurality of subjects and at least some of the study design information to the trained second machine learning model to produce the predicted retention rate for the clinical trial.

12. The computer platform of claim 11, wherein the at least one processor is further configured to perform:
applying the predicted retention rate to a third trained machine learning model to predict an overall success score of the clinical trial.

13. The computer platform of claim 8, wherein the at least one processor is further configured to perform:
receiving a respective set of parameters and corresponding parameter values for each of the plurality of subjects for the clinical trial;
applying the corresponding parameter values for the each of the plurality of subjects and the study design information to the trained first machine learning model to calculate a respective predicted travel score indicative of a travel burden for the each of the plurality of subjects;
calculating an average travel score for the plurality of subjects of the clinical trial based on each of the respective predicted travel scores; and
predicting an overall clinical trial success score based, at least partly, on the average travel score.

14. The computer platform of claim 8, wherein:
the study design information is received from a second computer platform via a network.

15. A non-transitory computer program product for monitoring a clinical trial, the computer program product comprising one or more computer readable storage media having program instructions collectively stored on the one or more computer readable storage media, the program instructions executable by at least one processor of a computer platform to cause the computer platform to:
receive study design information for the clinical trial, the study design information including a set of parameters and corresponding parameter values related to travel constraints of a subject for the clinical trial;
create first training data including parameter values of actual clinical trials and actual travel scores related to participants of the clinical trials;
train a first machine learning model using the first training data, wherein the first machine learning model includes a first neural network and is trained to predict a travel score indicative of a travel burden, and wherein the travel burden indicates a level of difficulty of travel:
apply the study design information and the corresponding parameter values to the trained first machine learning model to calculate a predicted travel score indicative of the travel burden for the subject;
when the predicted travel score fails to satisfy a travel score threshold:
determine at least one suggestion for adjusting the predicted travel score, and
output the at least one suggestion for adjusting the predicted travel score;
train a second machine learning model using the first training data to produce a predicted retention rate for the clinical trial, wherein the second machine learning model includes a second neural network, and training the second machine learning model includes:
creating second training data including at least some of the first training data;
processing the second training data by the trained first machine learning model to produce training predicted travel scores;
creating third training data including the training predicted travel scores from the trained first machine learning model and at least some of the second training data; and
training the second machine learning model using the third training data to predict the retention rate;
determine the predicted retention rate for the clinical trial by producing predicted travel scores for a plurality of subjects for the clinical trial by the trained first machine learning model and process the predicted travel scores and parameter values for the plurality of subjects by the trained second machine learning model to produce the predicted retention rate; and
output the predicted travel score and the predicted retention rate.

16. The non-transitory computer program product of claim 15, wherein the determining the at least one suggestion for adjusting the predicted travel score further comprises the at least one processor causing the computer platform to:
determine which one or more parameter values are negatively affecting the predicted travel score; and
output information regarding the determined one or more parameter values.

17. The non-transitory computer program product of claim 15, wherein the set of parameters and the corresponding parameter values include one or more from a group of an age of the subject, a level of mobility of the subject, one or more modes of travel the subject can use to travel to and from a clinical trial facility, whether the subject must visit the clinical trial facility during the clinical trial, a number of clinical trial visits required by the subject, a distance for the subject to travel to reach the clinical trial facility, an expected amount of travel time for the subject to travel to and from the clinical trial facility, an expected travel cost for the subject to travel to and from the clinical trial facility, family income of the subject, traffic density related to travel by the subject to and from the clinical trial facility, whether the subject has residential computer access to clinical trial data collection resources, whether the subject owns a telephone, and climate for a given locale of the clinical trial facility during the clinical trial.

18. The non-transitory computer program product of claim 15, wherein the at least one processor causes the computer platform to:
receive a respective set of parameters and corresponding parameter values for each of the plurality of subjects for the clinical trial;
apply the corresponding parameter values for each of the plurality of subjects and the study design information to the trained first machine learning model to calculate a respective predicted travel score indicative of a travel burden for the each of the plurality of subjects; and
apply the respective predicted travel score for the each of the plurality of subjects and at least some of the study design information to the second machine learning model to produce the predicted retention rate for the clinical trial.

19. The non-transitory computer program product of claim 18, wherein the at least one processor causes the computer platform to:
  apply the predicted retention rate to a third trained machine learning model to predict an overall success score of the clinical trial.

20. The non-transitory computer program product of claim 15, wherein the at least one processor further causes the computer platform to:
  receive a respective set of parameters and corresponding parameter values for each of the plurality of subjects for the clinical trial;
  apply the corresponding parameter values for each of the plurality of subjects and the study design information to the first trained machine learning model to calculate a respective predicted travel score indicative of a travel burden for the each of the plurality of subjects;
  calculate an average travel score for the plurality of subjects of the clinical trial based on each of the respective predicted travel scores; and
  predict an overall clinical trial success score based, at least partly, on the average travel score.

* * * * *